(12) United States Patent
Paulussen et al.

(10) Patent No.: US 11,679,423 B2
(45) Date of Patent: Jun. 20, 2023

(54) INTEGRATED SYSTEM FOR REAL-TIME ANTI-FOULING AND BIOFOULING MONITORING

(71) Applicant: KONINKLIJKE PHILIPS N.V., Eindhoven (NL)

(72) Inventors: Elvira Johanna Maria Paulussen, Reppel-Bocholt (BE); Bart Andre Salters, Eindhoven (NL); Hermanus Johannes Borg, Eindhoven (NL); Roelant Boudewijn Hietbrink, Utrecht (NL); Eduard Matheus Johannes Niessen, Ittervoort (NL)

(73) Assignee: Koninklijke Philips N.V., Eindhoven (NL)

( * ) Notice: Subject to any disclaimer, the term of this patent is extended or adjusted under 35 U.S.C. 154(b) by 1273 days.

(21) Appl. No.: 16/089,467

(22) PCT Filed: Mar. 23, 2017

(86) PCT No.: PCT/EP2017/056899
§ 371 (c)(1),
(2) Date: Sep. 28, 2018

(87) PCT Pub. No.: WO2017/167629
PCT Pub. Date: Oct. 5, 2017

(65) Prior Publication Data
US 2020/0298292 A1 Sep. 24, 2020

(30) Foreign Application Priority Data

Mar. 31, 2016 (EP) ..................................... 16163248

(51) Int. Cl.
*B08B 17/02* (2006.01)
*B63B 59/04* (2006.01)
(Continued)

(52) U.S. Cl.
CPC ................ *B08B 17/02* (2013.01); *A61L 2/10* (2013.01); *B63B 59/04* (2013.01);
(Continued)

(58) Field of Classification Search
CPC ........... B08B 17/02; A61L 2/10; G01N 21/49; G01N 21/84; G01N 2021/8416;
(Continued)

(56) References Cited

U.S. PATENT DOCUMENTS 4,680,475 A 7/1987 Tansony et al.
5,308,505 A * 5/1994 Titus .......................... A61L 2/10
210/764
(Continued)

FOREIGN PATENT DOCUMENTS

WO 2007093374 A1 8/2007
WO WO-2007093374 A1 * 8/2007 ......... G01B 11/0616
(Continued)

OTHER PUBLICATIONS

"Biodiversity", Department of Conservation, New Zealand Government, Accessed Sep. 27, 2018, https://www.doc.govt.nz/biodiversity.
(Continued)

*Primary Examiner* — Tarifur R Chowdhury
*Assistant Examiner* — Roberto Fabian, Jr.

(57) ABSTRACT

The invention provides an anti-biofouling system (200) comprising an UV-emitting element (210), wherein the UV-emitting element (210) comprises a UV radiation exit window (230), wherein the UV-emitting element (210) at least partly encloses a light source (220) configured to provide UV radiation (221), wherein the UV radiation exit window (230) is configured to transmit at least part of the UV radiation (221) of the light source (220), wherein the UV radiation exit window (230) comprises an upstream window
(Continued)

side (231) and a downstream window side (232), wherein the UV-emitting element (210) also at least partly encloses an optical sensor (310) configured to sense radiation (421) emanating from the downstream window side (232) and configured to provide a corresponding optical sensor signal, wherein the anti-biofouling system (200) is further configured to provide said UV radiation (221) in dependence of said optical sensor signal.

20 Claims, 4 Drawing Sheets

(51) Int. Cl.
    *G01N 21/31*          (2006.01)
    *G01N 21/33*          (2006.01)
    *G01N 21/49*          (2006.01)
    *G01N 21/64*          (2006.01)
    *G01N 21/84*          (2006.01)
    *A61L 2/10*           (2006.01)

(52) U.S. Cl.
CPC ......... *G01N 21/3151* (2013.01); *G01N 21/33* (2013.01); *G01N 21/49* (2013.01); *G01N 21/6486* (2013.01); *G01N 21/84* (2013.01); *G01N 2021/3181* (2013.01); *G01N 2021/8416* (2013.01)

(58) Field of Classification Search
CPC ........... G01N 21/15; G01N 2201/0212; G01N 33/1886; G01N 33/1833; G01N 21/3151; G01N 21/33; G01N 2021/3181
See application file for complete search history.

(56) References Cited

U.S. PATENT DOCUMENTS

| | | | | |
|---|---|---|---|---|
| 5,929,453 | A * | 7/1999 | Andrews | G01N 33/1833 250/461.1 |
| 7,190,457 | B2 | 3/2007 | Tabacco et al. | |
| 9,550,005 | B2 * | 1/2017 | Lin | A61L 2/10 |
| 2010/0324455 | A1 * | 12/2010 | Rangel | A61B 5/6807 36/43 |
| 2011/0299095 | A1 * | 12/2011 | Morgan | G01B 11/245 356/614 |
| 2012/0050520 | A1 * | 3/2012 | Thoren | G02B 27/0006 348/81 |
| 2013/0048877 | A1 | 2/2013 | Thoren et al. | |
| 2014/0078584 | A1 | 3/2014 | Farr et al. | |
| 2014/0151538 | A1 * | 6/2014 | Syed | G01N 21/17 250/222.1 |
| 2015/0070691 | A1 * | 3/2015 | Deshpande | C25D 3/30 356/237.2 |
| 2017/0197693 | A1 | 7/2017 | Salters et al. | |

FOREIGN PATENT DOCUMENTS

| | | | | |
|---|---|---|---|---|
| WO | 2008045609 A2 | 4/2008 | | |
| WO | 2014039496 A2 | 3/2014 | | |
| WO | 2014060562 A1 | 4/2014 | | |
| WO | 2014170075 A1 | 10/2014 | | |
| WO | WO-2014170075 A1 * | 10/2014 | ............. | A61L 9/205 |
| WO | 2014188347 A1 | 11/2014 | | |
| WO | WO-2014188347 A1 * | 11/2014 | ............... | A61L 2/10 |
| WO | 2016000980 A1 | 1/2016 | | |
| WO | WO-2016000980 A1 * | 1/2016 | ............ | B63B 59/08 |

OTHER PUBLICATIONS

Fhornber, C. S., Kinlan, B. P., Graham, M. H. & Stachowicz, J. J. 2004 "Population ecology of the invasive kelp *Undaria pinnatifida* in California: environmental and biological controls on demography". Mar. Ecol. Prog. Ser. 268, 69-80.

Fornalik, M., "Detecting Biofouling in Food Processing Systems", Mar. 2008.

United States Department of Agriculture, Agricultural Research Service, https://www.ars.usda.gov/, Accessed Sep. 27, 2018.

Petrone, L. et al., "In situ ATR-IR spectroscopic and electron microscopic analyses of settlement secretions of *Undaria pinnatifida* kelp spores", Journal of the Royal Society, 2011, pp. 410-422.

Albuquerque, I. et al., "Evaluation of Anti-Nociceptive and Anti-Inflammatory Activities of a Heterofucan from Dictyota nenstrualis", Marine Drugs, 2013, 11(8), pp. 2722-2740.

Fischer, M. et al., "Fluorescence-Based Quasicontinuous and In Situ Monitoring of Biofilm Formation Dynamics in Natural Marine Environments", Jun. 2014, vol. 80, No. 12, Applied and Environmental Microbiology p. 3721-3728.

Gitelson, A. et al., "Comparative reflectance properties of algal cultures with manipulated densities", Journal of Applied Phycology, 11: 345-354, 1999.

Evans, L., "Marine Algae and Fouling: A Review, with Particular Reference to Ship-Fouling", Botanica Marina, vol. XXIV, pp. 167-171, 1981.

* cited by examiner

INTEGRATED SYSTEM FOR REAL-TIME ANTI-FOULING AND BIOFOULING MONITORING

CROSS-REFERENCE TO PRIOR APPLICATIONS

This application is the U.S. National Phase application under 35 U.S.C. § 371 of International Application No. PCT/EP2017/056899, filed on 23 Mar. 2017, which claims the benefit of European Patent Application No. 16163248.4, filed on 31 Mar. 2016. These applications are hereby incorporated by reference herein.

FIELD OF THE INVENTION

The invention relates to an anti-biofouling system. The invention also relates to an object that during use is at least partly submerged in water, especially a vessel or an infrastructural object, which includes such anti-biofouling system. Further, the invention relates to a method for providing such anti-biofouling system to an object, especially a vessel or an infrastructural object.

BACKGROUND OF THE INVENTION

Anti-biofouling methods are known in the art. US2013/0048877, for instance, describes a system for anti-biofouling a protected surface, comprising an ultraviolet light source configured to generate ultraviolet light, and an optical medium disposed proximate to the protected surface and coupled to receive the ultraviolet light, wherein the optical medium has a thickness direction perpendicular to the protected surface, wherein two orthogonal directions of the optical medium orthogonal to the thickness direction are parallel to the protected surface, wherein the optical medium is configured to provide a propagation path of the ultraviolet light such that the ultraviolet light travels within the optical medium in at least one of the two orthogonal directions orthogonal to the thickness direction, and such that, at points along a surface of the optical medium, respective portions of the ultraviolet light escape the optical medium. US2012/050520 describes an apparatus and a method to prevent biofouling of underwater optical systems using ultraviolet light generated from within a pressure vessel and through an optics window, without removing the optical systems from the water and without disbursement of chemicals into the water. WO2016/000980 describes an anti-fouling lighting system configured for preventing or reducing biofouling on a fouling surface of an object that during use is at least temporarily exposed to a liquid, by providing an anti-fouling light to said fouling surface, the anti-fouling lighting system comprising: a lighting module comprising a light source configured to generate an anti-fouling light; and an energy system configured to locally harvest energy and configured to provide electrical power to said light lighting module, wherein the energy system comprises (i) a sacrificial electrode, and (ii) a second energy system electrode, wherein the energy system is configured to provide electrical power to the lighting module when the sacrificial electrode and the second energy system electrode are in electrical contact with the liquid. WO2007/093374 A1 describes a measuring system for determining a characteristic of a deposit that accumulates on the inside of a vessel wall, comprising: (a) at least one light-emitting unit, comprising a first structure which is integrated in the vessel wall and emits light into the vessel such that said light is scattered and/or reflected by said deposit, if any deposit is present, and (b) a detection unit, comprising a second structure which is integrated in the vessel wall and which is designed in such a manner that at least a portion of the light scattered and/or reflected by the deposit, if present, can pass from the interior of the vessel toward its exterior, and a light detector disposed such that its light-sensitive surface faces the second structure. WO2014/060562 A1 describes methods and systems for performing underwater surveys, in particular on sub-sea installations such as oil and gas pipelines, risers, well heads and so on. Further, this document describes an augmented underwater image of a scene for use in an underwater survey, using an underwater imaging system comprising a light module, image processing module and a camera module, the light module comprising a plurality of light classes each light class having one or more light sources. The document describes sequential imaging to provide the augmented output image. U.S. Pat. No. 5,308,505 A describes prevention of biofouling of underwater surfaces by marine organisms by irradiating the water with ultraviolet light and adjusting the intensity of the ultraviolet light so as to kill barnacle larvae to prevent their attachment to the underwater surface. The water is passed through a biocidal chamber having a source of ultraviolet light at an intensity of at least $4000\mu$ watts/cm$^2$ and at a rate to provide a residence time of at least one minute on the biocidal chamber.

SUMMARY OF THE INVENTION

Biofouling or biological fouling (herein also indicated as "fouling" or "biofouling") is the accumulation of microorganisms, plants, algae, and/or animals on surfaces. The variety among biofouling organisms is highly diverse and extends far beyond attachment of barnacles and seaweeds. According to some estimates, over 1700 species comprising over 4000 organisms are responsible for biofouling. Biofouling is divided into microfouling which includes bio film formation and bacterial adhesion, and macrofouling which is the attachment of larger organisms. Due to the distinct chemistry and biology that determine what prevents organisms from settling, these organisms are also classified as hard or soft fouling types. Calcareous (hard) fouling organisms include barnacles, encrusting bryozoans, mollusks, polychaete and other tube worms, and zebra mussels. Examples of non-calcareous (soft) fouling organisms are seaweed, hydroids, algae and biofilm "slime". Together, these organisms form a fouling community.

In several circumstances biofouling creates substantial problems. Machinery stops working, water inlets get clogged, and hulls of ships suffer from increased drag. Hence the topic of anti-fouling, i.e. the process of removing or preventing fouling from forming, is well known. In industrial processes, bio-dispersants can be used to control biofouling. In less controlled environments, organisms are killed or repelled with coatings using biocides, thermal treatments or pulses of energy. Non-toxic mechanical strategies that prevent organisms from attaching include choosing a material or coating with a slippery surface, or creation of nanoscale surface topologies similar to the skin of sharks and dolphins which only offer poor anchor points. Biofouling on the hull of ships causes a severe increase in drag, and thus increased fuel consumption. It is estimated that an increase of up to 40% in fuel consumption can be attributed to biofouling. As large oil tankers or container transport ships can consume up to €200.000 a day in fuel, substantial savings are possible with an effective method of anti-biofouling.

It surprisingly appears that one may effectively use UV radiation to substantially prevent biofouling on surfaces that are in contact with sea water or water in lakes, rivers, canals, etc. Herewith, an approach is presented based on optical methods, in particular using ultra-violet light or radiation (UV). It appears that most micro-organisms are killed, rendered inactive or unable to reproduce with sufficient UV light. This effect is mainly governed by the total dose of UV light. A typical dose to kill 90% of a certain micro-organism is 10 mW/h/m$^2$.

UV LEDs or UV sources may operate with limited wall plug efficiency and limited lifetime. This may limit the use of such light sources.

Hence, it is an aspect of the invention to provide an alternative system or method for prevention or reduction of biofouling, which preferably further at least partly obviates one or more of above-described drawbacks. In order to save energy and lifetime, it appears desirable to adapt the amount of UV radiation to the degree of fouling and/or even to the various types of fouling species. Amongst others, it is herein proposed to monitor the amount and/or sort of fouling and adapt the output power of the UV source for anti-fouling accordingly. For instance, the detection can be performed with a separate LED system, or a portion of the same radiation output of the source that is used for anti-fouling. In another embodiment, the emitted radiation consists of multiple wavelengths in order to distinguish the type of fouling and adapt the output power for anti-fouling depending on the specific organism. In yet a further embodiment, the sensor controls the LED power directly.

A specific implementation is to use the LEDs used for anti-fouling as sensor.

Amongst others, the invention provides solutions of integrating the fouling sensor system into an antifouling system layer and a new methodology to control the anti-fouling system with the sensor output.

In a first aspect, the invention provides an anti-biofouling system ("system") comprising a radiation emitting element (with the radiation selected from one or more of UV, visible and IR), especially an UV-emitting element, wherein the radiation emitting element, especially the UV-emitting element, comprises a radiation exit window, especially a UV radiation exit window ("exit window" or "window"), wherein the radiation emitting element, especially the UV-emitting element, at least partly encloses a light source configured to provide radiation (selected from one or more of UV, visible and IR), especially (at least) UV radiation, wherein the radiation exit window, especially the UV radiation exit window, is configured to transmit at least part of the radiation, especially the UV radiation, of the light source, wherein the radiation exit window, especially the UV radiation exit window, comprises an upstream window side and a downstream window side, wherein the radiation emitting element, especially the UV-emitting element, also at least partly encloses an optical sensor ("sensor") configured to sense radiation emanating from the downstream window side and configured to provide a corresponding optical sensor signal, wherein especially the anti-biofouling system is further configured to provide said radiation, especially said UV radiation, in dependence of said optical sensor signal, as further defined in the accompanying claims. The radiation emitting element may also be indicated as "element", or as "lighting module". A term "UV-emitting element" especially refers to a UV-radiation emitting element, i.e. an element configured to provide UV radiation.

In yet a further aspect, the invention also provides an object that during use is at least partly submerged in water, the object comprising the anti-biofouling system as described herein, wherein the radiation emitting element, especially the UV-emitting element, is configured to irradiate with radiation (selected from one or more of UV, visible and IR), especially (at least) UV radiation, during an irradiation stage one or more of (i) (a part of) an external surface of said object and (ii) water adjacent to said part of said external surface. In embodiments, the object may be selected from the group consisting of a vessel and an infrastructural object. The invention is further especially explained with reference to the anti-biofouling system in combination with the object.

With the present anti-biofouling system energy consumption may be reduced, and lifetime of the system, especially of the light source(s), may be improved. With the present system, it may also be possible to control the spectral distribution of the (UV) light and/or the intensity of the (UV) light as function of the fouling species to be combatted (and/or prevented) or to be detected, especially at least to be combatted (and/or prevented). In this way, more efficiently biofouling may be reduced. Further, the present invention provides in embodiments UV-emitting elements that may provide UV radiation in dependence of the position where the UV element is provided, or even in dependence of local biofouling. Also in this way, in a more efficient way biofouling may be reduced. Hence, an optimized anti-biofouling system is provided.

As indicated above, the anti-biofouling system comprises a UV-emitting element. The term "UV-emitting element" may also refer to a plurality of UV-emitting elements. Hence, the system may include a plurality of such elements. The system may include a source of electrical energy, but the system may (during use) also be functionally coupled with a source of electrical energy. In embodiments, each UV-emitting element may functionally be coupled with a source of energy. This allows a decentral powering of the UV-emitting elements. The source of energy is especially used for powering the light source(s).

Herein, the UV-emitting element can also be indicated as "lighting module". The UV-emitting element may be a plate-like module (herein also indicated as "optical medium"), with one or more relevant elements at least partly, or even entirely, embedded therein. Hence, in embodiments the UV-emitting element comprises light transmissive (solid) material, such as silicone, etc. However, the UV element may also include a housing enclosing at least partly, or even entirely, one or more relevant elements. The one or more relevant elements at least comprise the light source, which is configured to provide light source light, especially the UV radiation. The UV-emitting element may have a flat or a curved radiation exit window. The term "UV-emitting element" indicates that the element is especially configured to provide UV radiation during use of the element.

The UV-emitting element comprises a UV radiation exit window. The UV radiation exit window is configured to transmit at least part of the UV radiation of the light source. Hence, the exit window is transmissive for UV radiation. In general, the window will also be transmissive for visible light. As indicated above, and as will further be explained below, in embodiments the element may be a radiation transmissive plate. In such instance, the window may be a face (or plane) of the element. In yet other embodiment, the element comprises a housing, which housing comprises such window. In such embodiments, the radiation exit window (also) comprises light transmissive (solid) material, such as silicone, etc. The term "radiation transmissive" refers to transmissive for radiation, especially for UV radiation and optionally also for visible radiation.

The UV radiation exit window comprises an upstream window side and a downstream window side. The terms "upstream" and "downstream" relate to an arrangement of items or features relative to the propagation of the light from a light generating means (here the especially the light source), wherein relative to a first position within a beam of light from the light generating means, a second position in the beam of light closer to the light generating means is "upstream", and a third position within the beam of light further away from the light generating means is "downstream". Hence, the upstream window side ("upstream side") is especially directed to the internal of the element and may receive, directly, or after internal reflection, light source light. The downstream window side ("downstream side") may especially be directed to the external of the element. This window side may e.g. (temporarily) be in contact with water during use of the system. Note that in plate-like embodiments of the element the upstream window side and a downstream window side may be both sides of the (same) edge (or plane). In embodiments where a housing is applied, the window may have a non-zero thickness between the upstream window side and a downstream window side.

The element also includes an optical sensor. The sensor is at least partly enclosed by the element, but may in embodiments even be entirely embedded therein. Hence, the optical sensor is configured, like the light source, at the upstream window side of the element. The optical sensor ("sensor") is configured to sense radiation emanating from the downstream window side (into the element). Further, the term "sensor" may also refer to a plurality of sensors, of which optionally two or more may be configured to sense different properties.

The sensor may be configured to sense radiation within the element, which radiation originates from the light source.

In embodiments, the system may be based on the principle of TIR (Total Internal Reflection). The light source may be configured to provide the UV radiation (and/or other type of radiation; see below) to the radiation exit window based on the principle of total internal reflection. Hence, in embodiments the optical sensor is configured to sense UV radiation (and/or other type of radiation; see below) reflected by said UV radiation exit window. When biofouling is available on the radiation exit window, especially on the downstream window side, more UV radiation (and/or other type of radiation; see below) may escape from the element. Hence, less UV radiation (and/or other type of radiation; see below) may reach the optical sensor. When less UV radiation (and/or other type of radiation; see below) is received by the sensor, the system may if possible increase the intensity for anti-biofouling with UV radiation. Hence, even more especially the anti-biofouling system may be configured to increase intensity of said UV radiation when the optical sensor senses a reduction in UV radiation (and/or other type of radiation; see below). The (UV) radiation may be reduced as a result of "frustrated TIR" due to biofouling (at the downstream side of the radiation exit window). The biofouling extracts light from the light exit window. Hence, in embodiments the (sensed) radiation originates from the light source.

In embodiments, the system may be based on surface scattering. The light source may be configured to provide the UV radiation (and/or other type of radiation; see below) to the radiation exit window directly, as the radiation is provided within the critical angle (i.e. at an angle with a normal to the radiation exit window equal to or smaller, especially smaller, than the critical angle). Note that total internal reflection is a phenomenon which occurs when a propagating wave strikes a medium boundary at an angle larger than a critical angle with respect to the normal to the surface. Hence, in embodiments the light source is configured to provide at least part of said UV radiation (and/or other type of radiation; see below) within a total internal reflection critical angle with said radiation exit window and the optical sensor is configured to sense scattered UV radiation (and/or other type of scattered radiation; see below) (scattered by biofouling at said the (UV) radiation exit window). When biofouling is available on the radiation exit window, especially on the downstream window side, more UV radiation (and/or other type of radiation; see below) may be scattered back into the element. Hence, more UV radiation (and/or other type of radiation; see below) may reach the optical sensor. When more UV radiation (and/or other type of radiation; see below) is received by the sensor, the system may if possible increase the intensity for anti-biofouling with UV radiation. Hence, even more especially the anti-biofouling system is configured to increase intensity of said UV radiation when the optical sensor senses an increase in UV radiation (and/or other type of radiation; see below). Hence, in embodiments the (sensed) radiation originates from the light source. The scattering (like one or more of intensity and spectral distribution of the scattering radiation) may be characteristic for the biofouling species. Blue algae, for example, are blue because they scatter blue light (and absorb other wavelengths).

Alternatively or additionally, the optical sensor may be configured to sense luminescence (sometimes also indicated as "fluorescence") from species adjacent to or attached to the radiation exit window, especially the downstream window side. These species may emit radiation in the visible or infrared (IR) due to the irradiation with the UV radiation of the light source. This luminescence may enter the element via the radiation exit window and also emanate from the upstream window face. Would the sensor be configured to sense light in the visible, then also the radiation exit window is especially transmissive for visible light and/or would the sensor be configured to sense IR, then also the radiation exit window is especially transmissive for IR. Hence, in embodiments the sensor is adapted to measure the auto-fluorescence emission of the biofouling. The luminescence may be characteristic for the biofouling species. In general "fluorescence" or "auto-fluorescence emission" is herein indicated as luminescence. When more luminescence is received by the sensor, the system may—if possible—increase the intensity for anti-biofouling with UV radiation. Hence, even more especially the anti-biofouling system is configured to increase intensity of said UV radiation when the optical sensor senses an increase in luminescence (and/or other type of radiation; see below). Alternatively or additionally, an increase or decrease in UV radiation may (also) be dependent upon (a change in) the spectral distribution of the luminescence.

The element at least comprises a light source for UV radiation. This UV radiation is used for anti-biofouling. Hence, the UV radiation is used as anti-biofouling radiation. This radiation can also be the basis for the sensor, as the sensor may be configured to sense one or more of reflected UV radiation, scattered UV radiation, and luminescence (from species adjacent to or attached to the radiation exit window). Hence, in embodiments when using LEDs, the same LED wavelength is used for monitoring and anti-fouling. Hence, the source of the sensor system may in embodiments be a UV LED that is also used for anti-biofouling.

However, alternatively or additionally, a separate light source, herein also indicated as second light source, configured for generating second light source radiation ("second radiation"), can be the basis for the sensor. In such embodiments, the sensor may be configured to sense one or more of reflected second radiation, scattered second radiation, and luminescence (from species adjacent to or attached to the radiation exit window) due to excitation with second radiation. Hence, the source of the sensor system may be a UV LED (or laser) not substantially used for anti-biofouling. The source of the sensor system may also be a visible LED (or laser). Alternatively or additionally, the source of the sensor system may be an infrared LED (or laser). Hence, in the embodiments above it is referred to UV radiation and/or other type of radiation.

Herein, the term "light" in light source and similar terms may thus also refer to UV radiation and/or IR radiation (and of course visible light). This will be clear from the context.

As indicated above, the sensor is configured to provide a corresponding optical sensor signal. Hence, the sensor signal is especially related to the radiation that is sensed by the sensor and for which the sensor is configured. For instance, an increase in reflected (UV) radiation may e.g. relate to a larger sensor signal. Also, for instance an increase in scattered (UV) light may e.g. relate to a larger sensor signal. However, as indicated below, the sensor signal may also depend upon a (change in the) spectral distribution of the sensed light. Especially, the anti-biofouling system is further configured to provide said UV radiation (for anti-biofouling) in dependence of said optical sensor signal. Hence, when based on the sensor signal the system decides that there is biofouling, or (the amount of) biofouling is increasing, anti-biofouling light may be provided and/or increased (by the system). Alternatively or additionally, also the spectral distribution of the anti-biofouling light may be changed in dependence of the sensor signal (see also below).

The control loop described herein may include a control system, which may be integrated in the element, or which may be configured external from the element. In the latter embodiment, this implies a wired or wireless communication between the element and the control system. Hence, especially the object, or the anti-biofouling system, may further comprise a control system. Hence, the object comprises such control system, which may optionally be integrated in the anti-biofouling system, or elsewhere in the object. Therefore, in embodiments the anti-biofouling system may further comprise a control system enclosed by the UV-emitting element.

In an embodiment, the control system comprises a plurality of control systems. For instance, the vessel may comprise a control system, as master control system, with each anti-biofouling system comprising a slave control system. Optionally, the control system may be configured external form the object, i.e. remote from the object. In a specific embodiment, a master control system, remote from the object, controls the slave control system comprised by the object, (such as the anti-biofouling system). Hence, for instance the (master) control system may be far away; or not on the vessel, but ashore, such as in a control room of a shipping company. Such master control system may be configured to control anti-biofouling systems of a plurality of objects.

The control loop described herein may alternatively or additionally also include (relative simple) electronics (without a (temporary) memory). For instance, the system may include a radiation sensitive resistance. Such radiation sensitive resistance may be configured in an electrical circuit, including the light source, such that the anti-biofouling system is configured to provide said UV radiation in dependence of said optical sensor signal. Here, the sensor signal may be the (change in) resistance of the radiation sensitive resistance. The optical sensor may be sensitive to one or more of UV radiation, visible radiation and IR radiation. Such sensitivity may refer to a subrange of wavelengths within one (or more) of these, for instance an optical sensor substantially only sensitive in the wavelength range of 200-300 nm.

Here below, some further embodiments are discussed in more detail.

As indicated above, the UV radiation used for anti-fouling may also be used for sensing the extent of bio-fouling on the radiation exit window. Hence, in embodiments the anti-biofouling system is further configured to control the intensity of said UV radiation in dependence of said optical sensor signal.

The anti-biofouling system may control the UV radiation in dependence of one or more of the intensity of the radiation sensed by the sensor and the spectral distribution of the radiation sensed by the sensor. Hence, the anti-biofouling system may also be configured to determine the type of biofouling adjacent to or on the radiation exit window. For instance, the spectral distribution of the reflected or scattered light may depend upon the biofouling species. Alternatively or additionally, the spectral distribution of a luminescence (e.g. visible and/or IR) may be indicative of the biofouling species. Hence, when the light source also has a variable spectral distribution, this may be used to address specific biofouling species, as different species may have different absorption spectra (and (thus) different spectral positions where the species may be vulnerable to (UV) radiation). Note that the term light source may also relate to a plurality of (different) light sources, which may thus provide two or more different spectral distributions, thereby allowing tunability (of the radiation wavelength). Hence, in embodiments the light source has a variable spectral distribution of the UV radiation, and the anti-biofouling system is further configured to control the spectral distribution of said UV radiation in dependence of said optical sensor signal. Additionally (or alternatively), in embodiments the light source has a variable power.

As indicated above, not only the UV radiation may be used as basis for the sensor, alternatively or additionally other type of radiation may be applied. This radiation may be provided by the same light source that provides the UV radiation or by a separate light source (second light source). Hence, in embodiments (i) the light source is configured to provide UV radiation and one or more of visible and infrared radiation, and/or (ii) the UV-emitting element comprises a second light source configured to generate one or more of visible and infrared radiation, and wherein the optical sensor is configured to sense one or more of visible and infrared radiation and provide said corresponding sensor signal. Especially, in embodiments the anti-biofouling system is further configured to control one or more of the spectral distribution and the intensity of said UV radiation (and/or one or more of visible and infrared radiation) in dependence of a spectral distribution of the received radiation. This sensor may measure scattered and/or reflected visible and/or IR radiation. As indicated herein, there may be a (physical) blockade between the sensor and light source, to prevent the sensor receiving direct light source light from this light source.

Therefore, in embodiments the optical sensor is configured to sense said UV radiation. Alternatively or additionally, in embodiments the optical sensor is configured to sense one or more of visible and infrared radiation.

Especially, the system comprises a plurality of UV light sources. Even more especially, these may essentially be arranged in a regular pattern. Likewise, the system may include a plurality of sensors (which may essentially be arranged in a regular pattern). In general, an element may include more light sources than sensors, such as a plurality of light sources, but a single sensor, though optionally the element may also include a plurality of sensors. The distances between light sources may be smaller than the distances between the sensors.

Especially, the system may include a plurality of subsets, with each subset a plurality of light sources and one or more sensors. Hence, in embodiments the anti-biofouling system comprises a plurality of light sources, wherein neighboring light sources have mutual light source distances (d1) selected from the range of 0.5-200 mm, such as 2-100 mm, wherein the anti-biofouling system further comprises a plurality of optical sensors, wherein neighboring optical sensors have mutual optical sensor distances (d2) selected from the range of at least 0.5 mm, such as at least 2 mm, like at least 1 cm, such as at least 4 cm, like in the range of 0.5-200 mm. In specific embodiments, the anti-biofouling system comprises a plurality of subsets of light sources and optical sensors, wherein each subset comprises one or more light sources and one or more optical sensors, wherein each subset is configured to provide said UV radiation of the one or more light sources in the subset in dependence of optical sensor signal of the one or more optical sensors in the subset. In yet further embodiments, the biofouling system comprises a plurality of LEDs, wherein the LEDs are configured to generate said UV radiation, wherein the LEDs comprise LED dies, and wherein the LED dies of neighboring LEDs have mutual light source distances (d1) selected from the range of 0.5-200 mm, wherein the anti-biofouling system further comprises a plurality of optical sensors, wherein neighboring optical sensors have mutual optical sensor distances (d2) selected from the range of at least 0.5 mm, such as at least 2 mm, like at least 1 cm, such as at least 4 cm, like in the range of 0.5-200 mm, wherein the anti-biofouling system comprises a plurality of subsets of light sources and optical sensors, wherein each subset comprises one or more light sources and one or more optical sensors, wherein each subset is configured to provide said UV radiation of the one or more light sources in the subset in dependence of optical sensor signal of the one or more optical sensors in the subset. Especially d2>d1, such as d2/d1>2.

As indicated above, in a further aspect the invention provides an object that during use is at least partly submerged in water, the object comprising the anti-biofouling system as defined herein, wherein the UV-emitting element is configured to irradiate with UV radiation during an irradiation stage one or more of (i) a part of an external surface of said object and (ii) water adjacent to said part of said external surface. As indicated above, the object may especially be selected from the group consisting of a vessel and an infrastructural object.

Herein, the phrase "object that during use is at least partly submerged in water" especially refers to objects such as vessels and infrastructural objects that have aquatic applications. Hence, during use such object will be in general in contact with the water, like a vessel in the sea, a lake, a canal, a river, or another waterway, etc. The term "vessel" may e.g. refer to e.g. a boat or a ship, etc., such as a sail boat, a tanker, a cruise ship, a yacht, a ferry, a submarine, etc. etc. The term "infrastructural object" may especially refer to aquatic applications that are in general arranged substantially stationary, such as a dam, a sluice, a pontoon, an oilrig, etc. etc. The term "infrastructural object" may also refer pipes (for e.g. pumping up ocean water to e.g. a power plant), and other parts of (hydro-electrical) power plants, such as cooling systems, turbines, etc. The term "external surface" especially refers to the surface that may be in physical contact with water. In the case of pipes this may apply to one or more of the internal pipe surface and the external pipe surface. Hence, instead of the term "external surface" also the term "fouling surface" may be applied. Further, in such embodiments the term "water line" may also refer to e.g. filling level. Especially, the object is an object configured for marine applications, i.e. application in or near to a sea or an ocean. Such objects are during their use at least temporarily, or substantially always, at least partly in contact with the water. The object may be at least partly below the water (line) during use, or may substantially be all of its time below the water (line), such as for submarine applications. The invention may e.g. be applied for marine anti-fouling, keeping wetted surfaces clean, for off-shore applications, for (sub) sea applications, for drilling platforms, etc.

Due to this contact with the water, biofouling may occur, with the above indicated disadvantages. Biofouling will occur at the surface of an external surface ("surface) of such object. The surface of an (element of the) object to be protected may comprise steel, but may optionally also comprise another material, such as e.g. selected from the group consisting of wood, polyester, composite, aluminium, rubber, hypalon, PVC, glass fiber, etc. Hence, instead of a steel hull, the hull may also be a PVC hull or a polyester hull, etc. Instead of steel, also another iron material, such as an (other) iron alloys may be used Herein, the term "fouling" or "biofouling" or "biological fouling" are interchangeably used. Above, some examples of fouling are provided. Bio fouling may occur on any surface in water, or close to water and being temporarily exposed to water (or another electrically conductive aqueous liquid). On such surface biofouling may occur when the element is in, or near water, such as (just) above the water line (like e.g. due to splashing water, such as for instance due to a bow wave). Between the tropics, biofouling may occur within hours. Even at moderate temperatures, the first (stages of) fouling will occur within hours; as a first (molecular) level of sugars and bacteria.

The anti-biofouling system comprises at least an UV-emitting element. Further, the anti-biofouling system may comprise a control system (see also below), an electrical energy supply, etc.

The term "anti-biofouling system" may also refer to a plurality of such systems, optionally functionally coupled to each other, such as e.g. controlled via a single control system. Further, the anti-biofouling system may comprise a plurality of such UV-emitting elements. Herein, the term "UV-emitting element" may (thus) refer to a plurality of UV-emitting elements. For instance, in an embodiment a plurality of UV-emitting elements may be associated to an external surface of the object, such as a hull, or may be comprised by such surface (see also below), whereas e.g. a control system may be configured somewhere within the object, such as in a control room or wheel house of a vessel.

The surface or area on which fouling may be generated is herein also indicated as fouling surface. It may e.g. be the hull of a ship and/or an emission surface of an optical medium (see also below). To this end, the UV-emitting element provides UV radiation (anti-fouling light) that is applied to prevent formation of biofouling and/or to remove biofouling. This UV radiation (anti-fouling light) especially at least comprises UV radiation (also indicated as "UV light"). Hence, the UV-emitting element is especially configured to provide UV radiation. Thereto, the UV-emitting element comprises a light source. The term "light source" may also relate to a plurality of light sources, such as 2-20 (solid state) LED light sources, though many more light sources may also be applied. Hence, the term LED may also refer to a plurality of LEDs. Especially, the UV-emitting element may comprise a plurality of light sources. Hence, as indicated above, the UV-emitting element comprises one or more (solid state) state light sources. The LEDs may be (OLEDs or) solid state LEDs (or a combination of these LEDs). Especially, the light source comprises solid state LEDs. Hence, especially, the light source comprises a UV LED configured to provide one or more of UV-A and UVC light (see also below). UV-A may be used to impair cell walls, whereas UVC may be used to impair DNA. Hence, the light source is especially configured to provide the UV radiation. Herein, the term "light source" especially refers to a solid state light source. The light source(s) may also include (a) solid state laser(s).

Especially, the sensor is radiationally coupled with a light source (or a plurality of light sources). The term "radiationally coupled" especially means that the light source and the sensor are associated with each other so that at least part of the radiation emitted by the light source may be received by sensor via internal reflection (at the radiation exit window). Alternatively or additionally, the term "radiationally coupled" especially means that the light source and the sensor are associated with each other so that at least part of the radiation emitted by the light source may be received by sensor via scattering (at the radiation exit window). Alternatively or additionally, the term "radiationally coupled" especially means that the light source and the sensor are associated with each other so that at least part of the luminescence generated by a biofouling species upon radiation emitted by the light source may be received by sensor (via the radiation exit window). Hence, the invention provides a sensor system comprising the sensor and a light source, which light source may in embodiments be the light source used for generating UV radiation (and optionally other type or radiation) and/or which light source may be a second light source (not especially dedicated to provide anti-biofouling radiation). During use, the intensity of the radiation of the light source that may be the basis for the sensor may change with time (e.g. decreasing performance) and/or with temperature, etc. Therefore, it may be desirable to correct for this effect. Hence, in embodiments the anti-biofouling system further includes a control element configured (i) to correct the sensor signal for a dependency on the radiation intensity of the light source, such as for a dependency on the UV radiation intensity of a UV light source and/or (ii) configured to minimize variations in the radiation intensity of the light sources, such as to minimize variations in the UV radiation intensity of a UV light source. For instance, when the intensity of the radiation of the light source user for the sensor decreases with time, a sensor system may correct for this. In the latter variant, when the anti-biofouling system detects e.g. a decrease in light source intensity, the system may increase its intensity to a predetermined level. Such control may especially be used when the intensity change is not due to aging, but e.g. due to temperature differences. In embodiments, the light source and the sensor are not in a direct line of sight of each other. Hence, in embodiments radiation of the light source may only arrive at the sensor after at least one reflection. For instance, a physical blockade may be configured between the light source and sensor, to prevent direct light of the light source on the sensor.

Especially, the light source or the light sources is (are) LEDs. Hence, in embodiments the anti-biofouling system comprises a plurality of light sources, wherein the light sources comprise LEDs. Alternatively or additionally, the light sources comprise solid state lasers.

Ultraviolet (UV) is that part of electromagnetic light bounded by the lower wavelength extreme of the visible spectrum and the X-ray radiation band. The spectral range of UV light is, by definition between about 100 and 400 nm (1 nm=$10^{-9}$ m) and is invisible to human eyes. Using the CIE classification the UV spectrum is subdivided into three bands: UVA (long-wave) from 315 to 400 nm; UVB (medium-wave) from 280 to 315 nm; and UVC (short-wave) from 100 to 280 nm. In reality many photobiologists often speak of skin effects resulting from UV exposure as the weighted effect of wavelength above and below 320 nm, hence offering an alternative definition.

A strong germicidal effect is provided by the light in the short-wave UVC band. In addition erythema (reddening of the skin) and conjunctivitis (inflammation of the mucous membranes of the eye) can also be caused by this form of light. Because of this, when germicidal UV-light lamps are used, it is important to design systems to exclude UVC leakage and so avoid these effects. In case of immersed light sources, absorption of UV light by water may be strong enough that UVC leaking is no problem for humans above the liquid surface. Hence, in an embodiment the UV radiation (anti-fouling light) comprises UVC light. In yet another embodiment, the UV radiation comprises radiation selected from a wavelength range of 100-300 nm, especially 200-300 nm, such as 230-300 nm. Hence, the UV radiation may especially be selected from UVC and other UV radiation up to a wavelength of about 300 nm. Good results are obtained with wavelengths within the range of 100-300 nm, such as 200-300 nm.

As indicated above, the UV-emitting element is configured to irradiate with said UV radiation (during an irradiation stage) one or more of (i) said part of said external surface and (ii) water adjacent to said part of said external surface. The term "part" refers to part of the external surface of an object, such as e.g. a hull or a sluice (door). However the term "part" may also refer to substantially the entire external surface, such as the external surface of the hull or sluice. Especially, the external surface may comprise a plurality of parts, which may be irradiated with the UV light of one or more light sources, or which may be irradiated with the UV radiation of one or more UV-emitting elements. Each UV-emitting element may irradiate one or more parts. Further, there may optionally be parts that receive UV radiation of two or more UV-emitting elements.

In general, there may be distinguished between two main embodiments. One of the embodiments includes the part of the external surface being irradiated with the UV radiation with between the light source and UV-emitting element water (or air when above the water line), such as sea water, at least during the irradiation stage. In such embodiment, the part is especially comprised by the "original" external surface of the object. However, in yet another embodiment, the "original" external surface may be extended with a module, especially a relatively flat module, that is attached to the "original" external surface of the object (such as the hull of a vessel), whereby the module itself forms in fact the external surface. For instance, such module may be associated to the hull of a vessel, whereby the module forms (at least part of) the external surface. In both embodiments the UV-emitting element especially comprises a radiating exit surface (see further also below). However, especially in the latter embodiment wherein the UV-emitting element may provide part of said external surface, such radiation exit window may provide the part (as the first part and the radiation exit window may essentially coincide; especially may be the same surface).

Hence, in an embodiment the UV-emitting element is attached to said external surface. In yet a further specific embodiment the radiation exit window of the anti-biofouling system is configured as part of said external surface. Hence, in some of the embodiments the object may comprise a vessel comprising a hull, and the UV-emitting element is attached to said hull. The term "radiation exit window" may also refer to a plurality of radiation exit windows (see also below).

In both general embodiments, the UV-emitting element is configured to irradiate with said UV radiation (during an irradiation stage) water adjacent to said part of said external surface. In the embodiments wherein the module itself forms in fact the external surface, the UV-emitting element is at least configured to irradiate with said UV radiation (during an irradiation stage) said part of said external surface, as it is in fact part of said external surface, and optionally also water adjacent to said part of said external surface. Hereby, biofouling may be prevented and/or reduced.

In an embodiment, a significant amount of a protected surface to be kept clean from fouling, preferably the entire protected surface, e.g. the hull of a ship, may be covered with a layer that emits germicidal light ("anti-fouling light"), in particular UV light.

In yet another embodiment, the UV radiation (anti-fouling light) may be provided to the surface to be protected via a waveguide, such as a fiber.

Hence, in an embodiment the anti-fouling lighting system may comprise an optical medium, wherein the optical medium comprises a waveguide, such as an optical fiber, configured to provide said UV radiation (anti-fouling light) to the fouling surface. The surface of e.g. the waveguide from which the UV radiation (anti-fouling light) escapes is herein also indicated as emission surface. In general, this part of the waveguide may at least temporarily be submerged. Due to the UV radiation (anti-fouling light) escaping from the emission surface, an element of the object that is during use at least temporarily exposed to the liquid (such as seawater), may be irradiated, and thereby anti-fouled. However, the emission surface per se may also be anti-fouled. This effect is used in some of the embodiments of the UV-emitting element comprising an optical medium described below.

Embodiments with optical media are also described in WO2014188347. The embodiments in WO2014188347 are herein also incorporated by reference as they are combinable with the control unit and/or water switch, and other embodiments, described herein.

As indicated above, the UV-emitting element may especially comprise a UV radiation exit window. Hence, in a specific embodiment the UV-emitting element comprises a UV radiation exit window, with the UV-emitting element especially being configured to provide said UV radiation downstream from said UV radiation exit window of said UV-emitting element. Such UV radiation exit window may be an optical window through which the radiation escapes from the UV-emitting element. Alternatively or additionally, the UV radiation exit window may be the surface of a waveguide. Hence, UV radiation may be coupled in the UV-emitting element into the waveguide, and escape from the element via a (part of a) face of the waveguide. As also indicated above, in embodiments the radiation exit window may optionally be configured as part of the external surface of the object.

Especially, the (solid state) light source is at least controllable between a first UV radiation level and a second UV radiation level, wherein the first UV radiation level is larger than the second UV radiation level (and wherein the second UV radiation level is smaller than the first radiation level or may even be zero). Hence, in an embodiment the light source can be switched off and can be switched on (during a radiation stage). Further, optionally also the intensity of the UV radiation may be controlled between these two stages, such as a stepwise or continuous UV radiation intensity control. Hence, the light source is especially controllable (and thus its UV radiation intensity is).

As indicated above, the object or the anti-biofouling system may comprise a plurality of radiation exit windows. In embodiments this may refer to a plurality of anti-biofouling systems. However, alternatively or additionally, in embodiments this may refer to an anti-biofouling system comprising a plurality of UV radiation emitting elements. Such anti-biofouling system may thus especially include a plurality of light sources for providing UV radiation. However, alternatively or additionally, in embodiments this may (also) refer to an UV-emitting element comprising a plurality of light sources configured to provide the UV radiation. Note that an UV-emitting element with a single UV radiation exit window may (still) include a plurality of light sources.

Especially when the UV-emitting element comprises a plurality of light sources and a plurality of UV radiation exit windows, especially with each of such surface addressed by one more light sources, and/or when the bio-fouling system comprises a plurality of UV-emitting elements, by a control of the light sources it is possible to address different parts of the external surface independently. Hence, by arranging the different UV radiation exit windows at different heights of the object (with the height especially defined during use of the object), it is possible to substantially only irradiate with UV radiation only those parts for which applies that one or more of the part and the UV radiation exit window are below the water (line).

Hence, in a specific embodiment the anti-biofouling system comprises a plurality of light sources, a plurality of radiation exit windows, and a plurality of said parts, wherein the plurality of light sources are configured to provide said UV radiation via said plurality of radiation exit windows to said plurality of parts, and wherein said plurality of parts are configured at different heights of the object. Especially, the control system may be configured to control the (solid state) light sources individually as function of said input information. For instance, in a specific embodiment the control system may be configured to control the light sources individually as function of the positions of the parts of the external surface relative to the water (i.e. the water line).

The anti-biofouling system is especially configured to provide UV radiation to the part of the object or to water adjacent to this part. This especially implies that during an irradiation stage the UV radiation is applied. Hence, there may optionally also be periods wherein no UV radiation is applied at al. This may (thus) not only be due to e.g. a control system switching of one or more of the UV-emitting elements, but may e.g. also be due to predefined settings such as day and night or water temperature, etc. For instance, in an embodiment the UV radiation is applied in a pulsed way.

Hence, in a specific embodiment or aspect, the anti-biofouling system is configured for preventing or reducing biofouling on a fouling surface of an object, that during use is at least temporarily exposed to water, by providing an anti-fouling light (i.e. UV radiation) to said fouling surface or water adjacent thereto. Especially, the anti-biofouling system may be configured to provide said anti-fouling light via an optical medium to said fouling surface, wherein the UV-emitting element further comprises (ii) said optical medium configured to receive at least part of the UV radiation (anti-fouling light), the optical medium comprising an emission surface configured to provide at least part of said UV radiation (anti-fouling light). Further, especially the optical medium comprises one or more of a waveguide and an optical fiber, and wherein the UV radiation (anti-fouling light) especially comprises one or more of UVB and UVC light. These waveguides and optical media are herein further not discussed in detail.

The optical medium may also be provided as a (silicone) foil for applying to the protected surface, the foil comprising at least one light source for generating anti-fouling light and a sheet-like optical medium for distributing the UV radiation across the foil. In embodiments the foil has a thickness in an order of magnitude of a couple of millimeters to a few centimeters, such as 0.1-5 cm, like 0.2-2 cm. In embodiments, the foil is not substantially limited in any direction perpendicular to the thickness direction so as to provide substantially large foil having sizes in the order of magnitude of tens or hundreds of square meters. The foil may be substantially size-limited in two orthogonal directions perpendicular to the thickness direction of the foil, so as to provide an anti-fouling tile; in another embodiment the foil is substantially size-limited in only one direction perpendicular to a thickness direction of the foil, so as to provide an elongated strip of anti-fouling foil. Hence, the optical medium, and even also the UV-emitting element, may be provided as tile or as strip. The tile or strip may comprise a (silicone) foil.

In an embodiment the UV-emitting element comprises a two-dimensional grid of light sources for generating UV radiation and the optical medium is arranged to distribute at least part of the UV radiation from the two-dimensional grid of light sources across the optical medium so as to provide a two-dimensional distribution of UV radiation exiting the light emitting surface of the light module. The two-dimensional grid of light sources may be arranged in a chicken-wire structure, a close-packed structure, a rows/columns structure, or any other suitable regular or irregular structure. The physical distance between neighboring light sources in the grid may be fixed across the grid or may vary, for example as a function of light output power required to provide the anti-fouling effect or as function of the location of the UV-emitting element on the protected surface (e.g. location on the hull of a ship). Advantages of providing a two-dimensional grid of light sources include that the UV radiation may be generated close to the areas to be protected with UV radiation illumination, and that it reduces losses in the optical medium or light guide and that it is increasing homogeneity of the light distribution. Preferably, the UV radiation is generally homogeneously distributed across the emission surface; this reduces or even prevents under-illuminated areas, where fouling may otherwise take place, while at the same time reducing or preventing energy waste by over-illumination of other areas with more light than needed for anti-fouling. In an embodiment, the grid is comprised in the optical medium. In yet another embodiment, the grid may be comprised by a (silicone) foil.

Further, in an embodiment the optical medium may be disposed proximate (including optionally attached to) to the protected surface and coupled to receive the ultraviolet light, wherein the optical medium has a thickness direction perpendicular to the protected surface, wherein two orthogonal directions of the optical medium orthogonal to the thickness direction are parallel to the protected surface, wherein the optical medium is configured to provide a propagation path of the ultraviolet light such that the ultraviolet light travels within the optical medium in at least one of the two orthogonal directions orthogonal to the thickness direction, and such that, at points along a surface of the optical medium, respective portions of the ultraviolet light escape the optical medium.

In a further aspect, the invention also provides a method of anti-(bio)fouling (a part of) an external surface of an object that is during use at least temporarily exposed to water, the method comprising: providing the anti-biofouling system as defined herein to the object, generating the UV radiation (during use of the object), optionally as function of one or more of (i) a feedback signal, and (ii) a timer for (periodically) varying the intensity of the UV radiation (anti-fouling light), and providing said UV radiation (during an irradiation stage) to (the part of) the external surface. Such feedback signal may be provided by the sensor.

In yet a further aspect, the invention also provides a method of providing an anti-biofouling system to an object, that during use is at least temporarily exposed to water, the method comprising providing, such as integrating in the object and/or attaching to an external surface, the anti-biofouling system to the object, such as a vessel, with the UV-emitting element configured to provide said UV radiation to one or more of a part of an external surface of the object and water (being) adjacent to said part (during use), as further defined in the accompanying claims. Especially, the UV-emitting element is attached to the external surface, or may even be configured as (first) part of the external surface.

The terms "visible", "visible light" or "visible emission" refer to light having a wavelength in the range of about 380-780 nm.

Hence, the invention provides in embodiments a biofouling sensor system to monitor and control biofouling on the surface of a transparent light guide, where the sensor system is embedded in the same light guide that transports the radiation for anti-fouling. The source of the sensor system may be a UV light source. The source of the sensor system may be a visible LED. The source of the sensor system may comprise multiple LEDs (i.e. blue and green). The source of the sensor system may be one or more infrared LED(s). Further, the source of the sensor system may essentially provide multiple wavelengths, with the sensor being adapted to measure emission (especially fluorescence), reflection and/or scattering spectra of the biofouling.

In specific embodiment, the same type of LED may be used as sensor. Hence, one or more LED sources may be configured in such way, that anti-fouling can be applied and that radiation can be converted into a signal with the same LED(s). This may imply that during certain time periods, the LEDs are in one mode (e.g. emitting), and during other time periods the LEDs are in the 'sensing mode'. Hence, sensing and emitting may periodically alternate with time. The LEDs function in certain time intervals in radiation emitting mode, and in other time intervals in radiation detecting mode. The wavelength sensitivity in detection mode may shift to slightly higher wavelengths (10-30 nm), which can help in sensing fluorescence.

In further embodiments, fouling levels on various areas of the anti-fouling surface can be detected and controlled separately.

In yet further embodiments, the monitoring takes place real-time and the fouling signal from the sensor is used to control the UV radiation of the anti-fouling system.

Hence, anti-biofouling radiation especially includes UV radiation. Radiation used for detection with the sensor (reflection, scattering, luminescence) may be one or more of UV, visible and IR radiation, i.e. especially substantially any radiation between about 200 and 1500 nm.

BRIEF DESCRIPTION OF THE DRAWINGS

Embodiments of the invention will now be described, by way of example only, with reference to the accompanying schematic drawings in which corresponding reference symbols indicate corresponding parts, and in which.

The drawings are not necessarily to scale.

DETAILED DESCRIPTION OF THE EMBODIMENTS

Figure 1A:
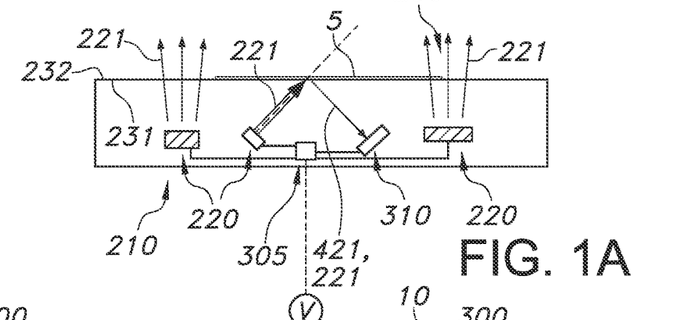
FIGS. 1a-1h schematically depict some general aspects.

FIG. 1a schematically depicts an embodiment of an anti-biofouling system which comprises an UV-emitting element 210. The UV-emitting element 210 comprises a UV radiation exit window 230. The UV-emitting element 210 at least partly encloses a light source 220 configured to provide UV radiation 221. Here, by way of example three light sources 220 are depicted. Here, the UV-emitting element 210 is configured as waveguide, with elements embedded therein. Hence, the light sources 220 are embedded in the waveguide. The UV radiation exit window 230 is configured to transmit at least part of the UV radiation 221 of the light source 220. The UV radiation exit window 230 comprises an upstream window side 231, here directed to the light source(s) and a downstream window side 232. The UV-emitting element 210 also at least partly encloses an optical sensor 310 configured to sense radiation 421 emanating from the downstream window side 232. Here, the sensor 310 is also embedded in the waveguide. The sensor 310 is configured to provide a corresponding optical sensor signal, corresponding to the radiation 421 emanating from the downstream side. Further, the anti-biofouling system 200 is further configured to provide said UV radiation 221 in dependence of said optical sensor signal. Radiation 421 may include one or more of scattering of light source radiation 221 (by biofouling at the downstream window side 232), reflection of light source radiation 221 (at the upstream window side 231), and luminescence of biofouling (at the downstream window side 232), indicated with reference 5.

Here, in this schematically depicted embodiment the same type of light source is used for anti-biofouling radiation 221 and for the control loop with the sensor 310; however, this is not necessarily the case. Reference 305 refers to electronics or a control element (see also below) for controlling the radiation 221 of the light sources 220 as function of the optical sensor 310. Here, controlling may refer to one or more of controlling the intensity and controlling the spectral distribution. The combination of sensor 310 and light source that generates radiation that is used directly or indirectly, such as by reflection, scattering, luminescence, is herein also indicated as sensor system. The light source is herein also indicated as source of the sensor system.

The term "controlling" especially refers to determining the behavior or supervising the running of the light source, especially thus one or more of the intensity and the spectral distribution, especially at least the intensity.

Figure 1B:
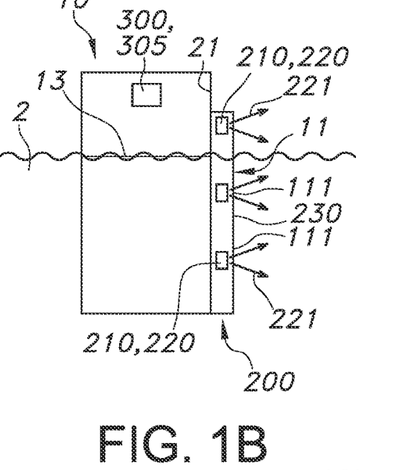

Note that in the embodiment schematically depicted in FIG. 1b and also other embodiments described herein and/or depicted herein include a radiation emitting element, especially here thus the UV emitting element 220, which encloses at least partly, or even substantially entirely, the light source and the sensor.

Figure 1C:
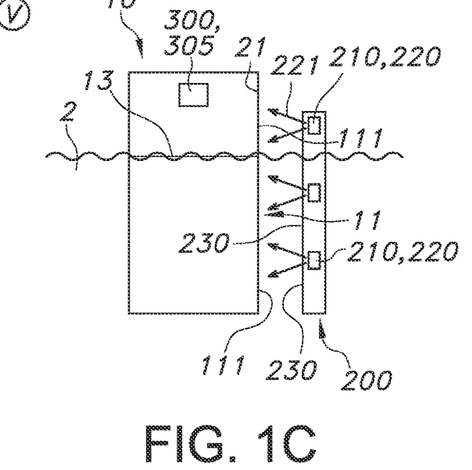
Figure 1D:
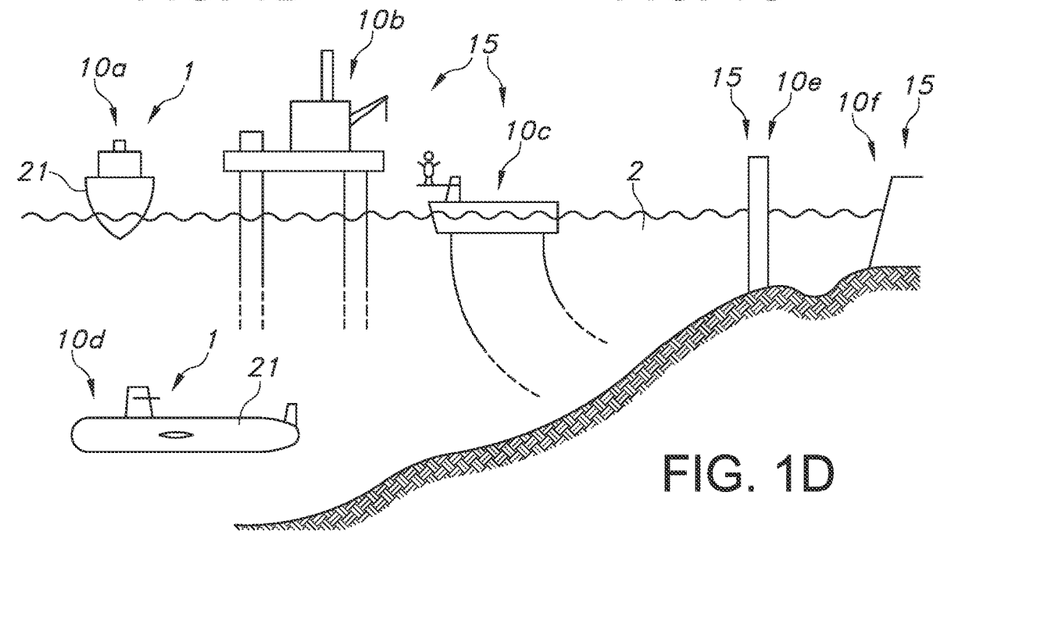

FIGS. 1b-1d schematically depict embodiments of an object 10 that during use is at least partly submerged in water 2, see the water line 13. The object 10, such as a vessel or a sluice, see also below, further comprises an anti-biofouling system 200 comprising an UV-emitting element 210, especially for application of UV radiation 221 to a part 111 of an external surface 11 of the object 10, such as a hull or part or a hull. Here, two embodiments are shown wherein the anti-biofouling system 200, or more especially the UV-emitting element 210 is part of an outer surface, and thereby forms in fact part of the outer surface (FIG. 1a) or wherein the UV-emitting element 210 is configured to irradiate the outer surface and does not necessarily form part of an outer surface, such as a hull of a ship (FIG. 1c). For instance, the object 10 is selected from the group consisting of a vessel 1 and an infrastructural object 15 (see also below).

The UV-emitting element 210 comprises one or more light sources 220 and may thus especially be configured to irradiate with said UV radiation 221 during an irradiation stage one or more of (i) said part 111 of said external surface 11 and (ii) water adjacent to said part 111 of said external surface 11. The former variant applies especially the embodiment of FIG. 1c, and the latter embodiment especially applies to both embodiments of FIGS. 1b-1c. Note however that when an external surface of the UV-emitting element 210 is configured as external surface of the object 10, of course the part 111 is irradiated per se with the UV radiation 21.

Hence, the UV-emitting element 210 comprises a UV radiation exit window 230 and the UV-emitting element 210 is configured to provide said UV radiation 221 downstream from said UV radiation exit window 230 of said UV-emitting element 210.

Especially, the light source 220 is at least controllable between a first UV radiation level and a second UV radiation level, wherein the first UV radiation level is larger than the second UV radiation level (and wherein the second UV radiation level is smaller than the first radiation level (including e.g. zero).

As indicated above, the term "vessel", indicated with reference 1, may e.g. refer to e.g. a boat or a ship (ref. 10a in FIG. 1d), etc., such as a sail boat, a tanker, a cruise ship, a yacht, a ferry, a submarine (ref 10d in FIG. 1d), etc. etc., like schematically indicated in FIG. 1d. The term "infrastructural object", indicated with reference 15, may especially refer to aquatic applications that are in general arranged substantially stationary, such as a dam/sluice (references 10e/10f in FIG. 1d), a pontoon (ref. 10c in FIG. 1d), an oilrig (ref. 10b in FIG. 1d), etc. etc.

Figure 1E:
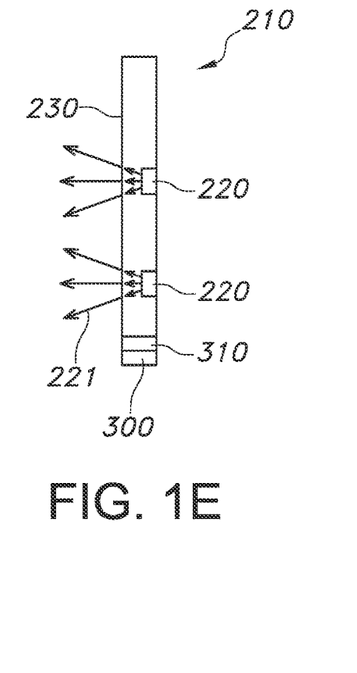

FIG. 1e schematically depicts in more detail an embodiment of a UV-emitting element 210 of an anti-biofouling system, here by way of example including an integrated control system 300 and an integrated sensor 310.

Figure 1F:
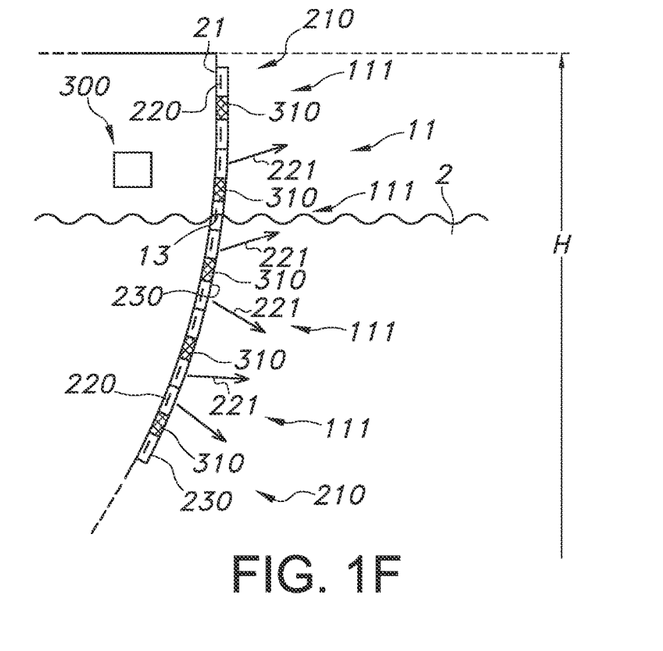

FIG. 1f schematically depicts an external surface 11 of an object, such as a vessel wall or a wall of an infrastructural object, with by way of example a plurality UV-emitting elements 210 (here associated to a hull 21 of a vessel). Alternatively or additionally, a plurality of functionally coupled or independently functioning anti-biofouling systems may be applied FIG. 1f also schematically depicts the embodiment wherein the anti-biofouling system comprises a plurality of UV-emitting elements 210 (with a plurality of light sources), a plurality of radiation exit windows 230, and a plurality of said parts 111, wherein the plurality of light sources 220 are configured to provide said UV radiation 221 via said plurality of radiation exit windows 230 to said plurality of parts 111, and wherein said plurality of parts 111 are configured at different heights of the object, and wherein the control system 300 is configured to control the light sources 220 individually as function of said input information. For instance, in an embodiment the control system 300 may be configured to control the light sources 220 individually as function of the positions of the parts 111 of the external surface 11 relative to the water.

Figure 1G:
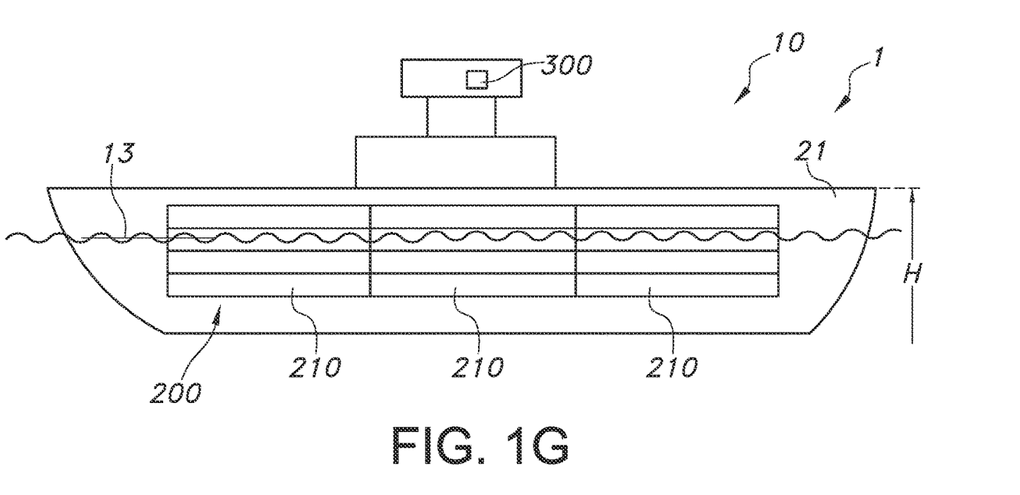

FIG. 1g schematically depicts an embodiment wherein a vessel 1, as embodiment of the object 10, comprises a plurality of anti-biofouling systems 200 and/or a one or more of such anti-biofouling systems 200 comprising a plurality of UV-emitting elements 210. Dependent upon the height of the specific such anti-biofouling system 200 and/or the height of the UV-emitting elements 210, such as relative to a water (line), the respective UV-emitting elements 210 may be switched on.

Figure 1H:
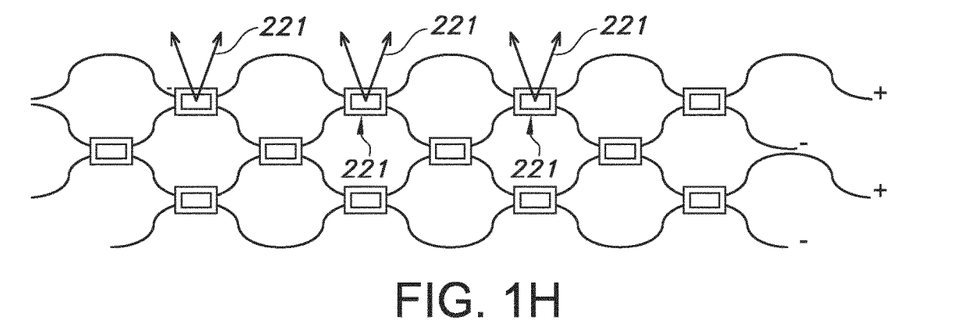

FIG. 1h shows a chicken-wire embodiment where light sources 210, such as UV LEDs, are arranged in a grid and connected in a series of parallel connections. The LEDs can be mounted at the nodes either through soldering, gluing or any other known electrical connection technique for connecting the LEDs to the chicken wires. One or more LEDs can be placed at each node. DC or AC driving can be implemented. If AC is used, then a couple of LEDs in anti parallel configuration may be used. The person skilled in the art knows that at each node more than one couple of LEDs in anti parallel configuration can be used. The actual size of the chicken-wire grid and the distance between UV LEDs in the grid can be adjusted by stretching the harmonica structure. The chicken-wire grid may be embedded in an optical medium. Above, especially active prevention applications are described, wherein the anti-biofouling system 200 switches off, or switches specific UV-emitting elements 210 or specific light sources 220 off, dependent upon contact with the water, a signal of a sensor, etc. etc. However, alternatively or additionally, also warning signals or messages may be used to warn a person of danger.

Figure 2A:
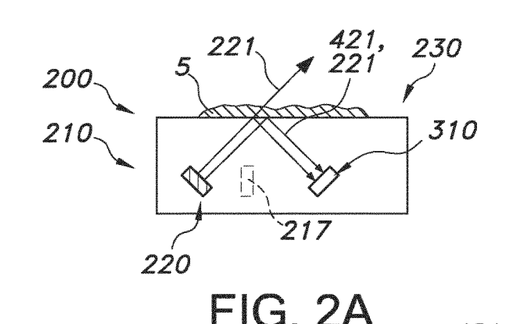
FIGS. 2a-2d schematically depict some embodiments and variants.
Figure 2B:
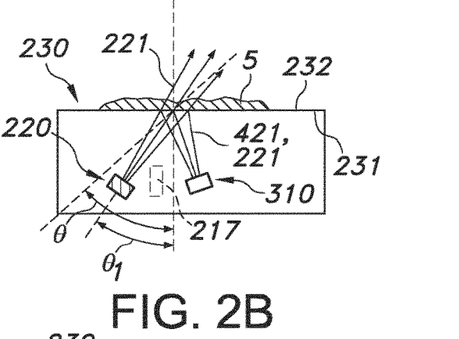

FIGS. 2a-2b schematically depict a variant wherein total internal reflection (TIR) and a variant wherein scattering are used as input for the sensor 310, respectively. The total internal reflection may decrease with increasing biofouling 5. The scattering may increase with increasing biofouling. Here, by way of example the light source 220, which is also used for the generation of UV radiation as anti-biofouling light is applied (in the sensor system); however, also an alternative light source may be applied (see also FIG. 2d). FIGS. 2a-2b by way of example also include a blocking element or physical blockade, indicated with reference 217 which is configured to prevent light source radiation, indicated with reference 221, to directly reach the sensor 310. Further, FIG. 2b schematically depicts a normal to the radiation exit window 230. The critical angle is indicated with θ; an optical axis of the light source radiation 221 has an angle $\theta_1$, and is thus within the critical angle. In FIG. 2a, this angle may (substantially) be larger, as use is made of TIR.

Figure 2C:
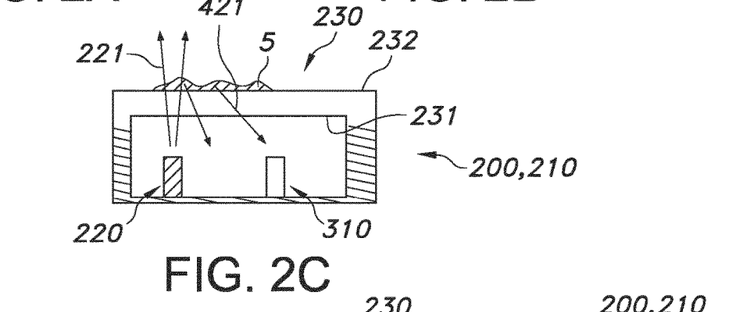

FIG. 2c schematically depicts an embodiment wherein luminescence of biofouling 5 is used. This luminescence may be in the visible and/or infrared. Excitation may be with the light source 220 or an alternative light source (see also FIG. 2d).

Here, by way of example a housing with a separate radiation exit window 230 is schematically depicted, instead of a waveguide plate as used in many of the other schematic drawings. Hence, the UV-emitting element may be a plate-like module, with one or more relevant elements at least partly, or even entirely, embedded therein. However, the UV element may also include a housing enclosing at least partly, or even entirely, one or more relevant elements. The one or more relevant elements at least comprise the light source, which is configured to provide light source radiation, especially the UV radiation.

Figure 2D:
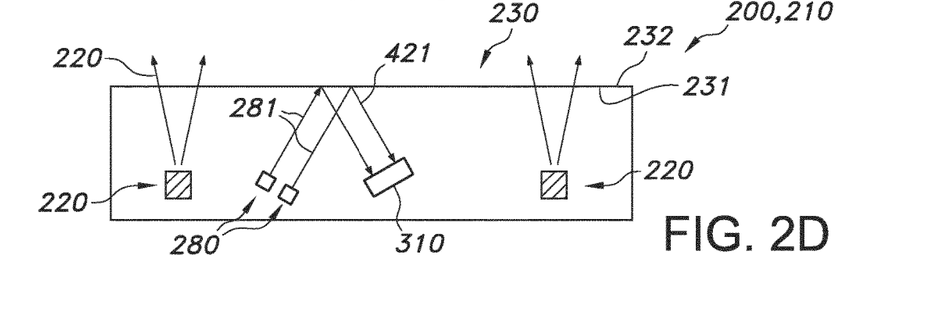

FIG. 2d schematically depicts an embodiment wherein the system 200 comprises a second light source 280 configured to generate one or more of visible and infrared radiation, herein indicated as second light source light 281, and wherein the optical sensor 310 is configured to sense one or more of visible and infrared radiation and provide said corresponding sensor signal. Here, by way of examples two second light sources 280 are applied, e.g. to provide different types of light, like blue and green, or visible and IR, etc. The optical sensor 310 may be configured to sense one or more of visible and infrared radiation and provide said corresponding sensor signal.

Note that when in addition when visible or IR radiation as input for the sensor system is desired, one may also use light sources 220 which are configured to provide UV radiation 221 and one or more of visible and infrared radiation.

Figure 3A:
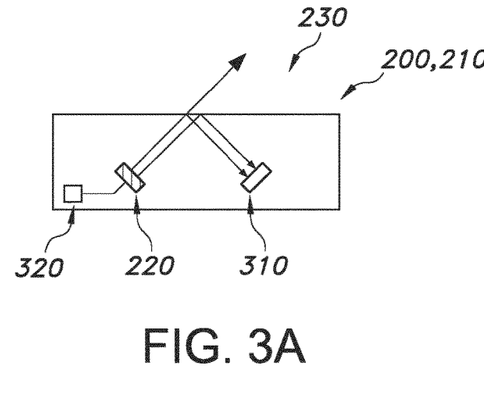
FIGS. 3a-3b schematically depict some further embodiments and variants.
Figure 3B:
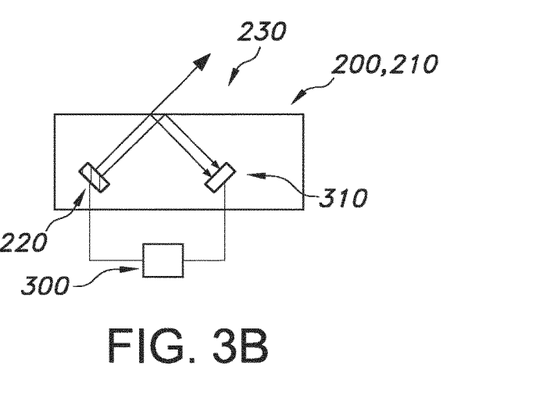

The anti-biofouling system 200 may further including a control element 320 configured to correct the sensor signal for a dependency on the UV radiation intensity of the light source 220. The control element 320 may also be configured to minimize variations in the UV radiation intensity of the light source 220, as schematically depicted in FIG. 3a. In embodiments, the control element 320 may be comprised by the control system 300 (not depicted in this schematical drawing).

Referring to FIGS. 2a-2d and 3a-3b, and other embodiments described herein but not depicted, the light source and the sensor are especially configured at the same side of the radiation exit window 230. Referring to FIGS. 2a-2d and 3a-3b, and other embodiments described herein but not depicted, the light source and the sensor are especially configured at the same side of the upstream window side 231.

It is further noted that (thus) the light source and optical sensor can both be embedded in the light emitting element, even more especially in the waveguide, such as a silicone waveguide.

The waveguide especially comprises a radiation transmissive material, such as glass, quartz, (fused) silica, silicone, fluoropolymer etc.

Figure 4A:
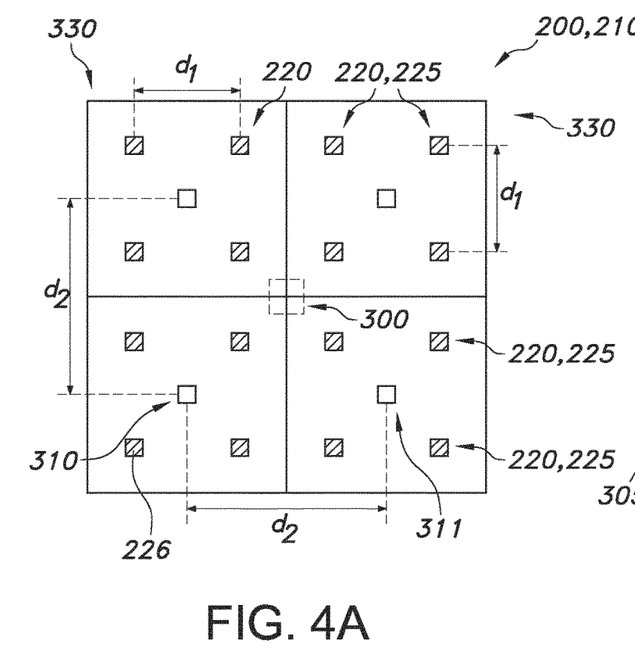
FIGS. 4a-4b schematically depict some further embodiments and variants.

FIG. 4a schematically depicts an embodiment of the anti-biofouling system 200 comprising a plurality of light sources 220. Here, the light sources 220 comprise LEDs 225. The LEDs comprise LED dies 226. The LED dies 226 of neighboring LEDs 225 have mutual light source distances d1, especially selected from the range of 0.5-200 mm. As shown, the anti-biofouling system 200 further comprises a plurality of optical sensors 310. Neighboring optical sensors have mutual optical sensor distances d2, especially selected from the range of at least 4 cm, such as in the range of 10-100 cm. Here, the anti-biofouling system 200 comprises a plurality of subsets 330 of light sources 220 and optical sensors 310, wherein each subset 330 comprises one or more light sources 220 and one or more optical sensors 310. Especially, each subset 330 is configured to provide said UV radiation 221 of the one or more light sources 220 in the subset 330 in dependence of optical sensor signal of the one or more optical sensors 310 in the subset 330. A control system may be included in one or more elements 210 or there may e.g. be a central control system 300, schematically indicated with the dashed square. Note that the control system 300 may also be remote from the elements 210.

Figure 4B:
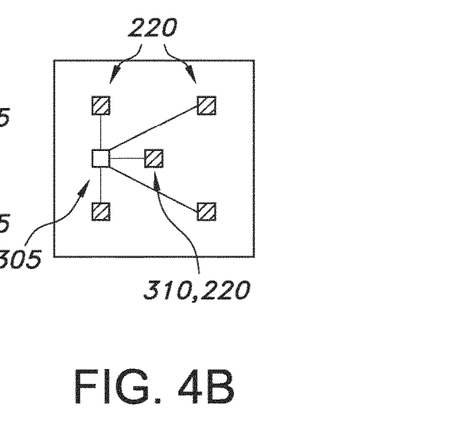

FIG. 4b schematically depicts an embodiment wherein a light source 220, i.e. here a solid state light source, is configured as sensor. To this end electronics or a control element 305 may be included to have the solid state light source function as sensor 310. Optionally, this light source may be controlled by the electronics or control element 305 to switch between a sensing stage and a radiation stage.

Electronics or a control element 305 may be comprised by a control system 300 (not depicted here).

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

The invention claimed is:

1. An anti-biofouling system comprising:
an UV-emitting element,
a light source, and
an optical sensor,
wherein the UV-emitting element comprises: a UV radiation exit window, wherein the UV-emitting element at least partly encloses the light source configured to provide UV radiation, wherein the UV radiation exit window is configured to transmit at least part of the UV radiation of the light source, wherein the UV radiation exit window comprises an upstream window side and a downstream window side, wherein the UV-emitting element also at least partly encloses the optical sensor configured to sense radiation emanating from the downstream window side and generated by the light source, and configured to provide a corresponding optical sensor signal, wherein the anti-biofouling system is further configured to provide said UV radiation in dependence of said optical sensor signal.

2. The anti-biofouling system according to claim 1, wherein the anti-biofouling system is configured to control an intensity of said UV radiation in dependence of said optical sensor signal.

3. The anti-biofouling system according to claim 1, wherein the light source has a variable spectral distribution of the UV radiation, and wherein the anti-biofouling system is configured to control the spectral distribution of said UV radiation in dependence of said optical sensor signal.

4. The anti-biofouling system according to claim 1, wherein the optical sensor is configured to sense UV radiation reflected by the UV radiation exit window, and wherein the anti-biofouling system is configured to increase an intensity of said UV radiation when the optical sensor senses a reduction in the reflected UV radiation.

5. The anti-biofouling system according to claim 1, wherein the light source is configured to provide at least part of said UV radiation within a total internal reflection critical angle with said radiation exit window, wherein the optical sensor is configured to sense scattered UV radiation from the downstream window side of the radiation exit window, and wherein the anti-biofouling system is configured to increase an intensity of said UV radiation when the optical sensor senses an increase in the scattered UV radiation.

6. The anti-biofouling system according to claim 1, wherein the light source is configured to provide UV radiation and one or more of visible and infrared radiation.

7. The anti-biofouling system according to claim 1, wherein the optical sensor is configured to sense said UV radiation.

8. The anti-biofouling system according to claim 1, wherein the optical sensor is configured to sense one or more of visible and infrared radiation.

9. The anti-biofouling system according to claim 1, wherein the anti-biofouling system is further configured to control one or more of a spectral distribution and an intensity of said UV radiation in dependence of a spectral distribution of the sensed radiation.

10. The anti-biofouling system according to claim 1, further including a control element configured (i) to correct the sensor signal for a dependency on an intensity of the UV radiation of the light source and/or (ii) to minimize variations in the UV radiation intensity of the light source.

11. The anti-biofouling system according to claim 1, further comprising a control system enclosed by the UV-emitting element.

12. The anti-biofouling system according to claim 1, comprising a plurality of light sources, wherein the light sources comprise LEDs.

13. The anti-biofouling system according to claim 12, wherein the LEDs are configured to generate said UV radiation, wherein the LEDs comprise LED dies, and wherein the LED dies of neighboring LEDs have mutual light source distances (d1) selected from the range of 0.5-200 mm, wherein the anti-biofouling system further comprises a plurality of optical sensors, wherein neighboring optical sensors have mutual optical sensor distances (d2) of at least 4 cm, wherein the anti-biofouling system comprises a plurality of subsets of light sources and optical sensors, wherein each subset comprises one or more light sources and one or more optical sensors, wherein each subset is configured to provide said UV radiation of the one or more light sources in the subset in dependence of the corresponding optical sensor signal of the one or more optical sensors in the subset.

14. An object that during use is at least partly submerged in water, the object comprising the anti-biofouling system according to claim 1, wherein the UV-emitting element is configured to irradiate with UV radiation during an irradiation stage one or more of (i) a part of an external surface of said object and (ii) water adjacent to said part of said external surface, wherein the object is selected from the group consisting of a vessel and an infrastructural object.

15. A method of providing an anti-biofouling system as defined in claim 1 to an object, that during use is at least temporarily exposed to water, the method comprising providing the anti-biofouling system to the object with the UV-emitting element configured to provide said UV radiation to one or more of a part of an external surface of the object and water adjacent to said part.

16. The anti-biofouling system of claim 6, wherein the optical sensor is configured to sense the one or more of visible and infrared radiation and is configured to provide said corresponding sensor signal in response to the one or more of visible and infrared radiation.

17. The anti-biofouling system of claim 1, comprising a second light source configured to generate one or more of visible and infrared radiation.

18. The anti-biofouling system of claim 17, wherein the optical sensor is configured to sense the one or more of visible and infrared radiation and is configured to provide said corresponding sensor signal in response to the one or more of visible and infrared radiation.

19. The object of claim 14, wherein the anti-biofouling system is configured to control an intensity of said UV radiation in dependence of said optical sensor signal.

20. The method of claim 15, further comprising controlling an intensity of said UV radiation in dependence of said optical sensor signal.

* * * * *